(12) United States Patent
Baker et al.

(10) Patent No.: US 10,810,908 B2
(45) Date of Patent: Oct. 20, 2020

(54) PREFILLED SYRINGE TRAINING DEVICE WITH RELEASEABLY LOCKING NEEDLE GUARD

(71) Applicant: NOBLE INTERNATIONAL, INC., Orlando, FL (US)

(72) Inventors: Jeff Baker, Orlando, FL (US); Francis Michael Siemer, Orlando, FL (US); Christopher Wai Yin Chung, Orlando, FL (US); Shishuang Hou, Ningbo (CN)

(73) Assignee: NOBLE INTERNATIONAL, INC., Orlando, FL (US)

( * ) Notice: Subject to any disclaimer, the term of this patent is extended or adjusted under 35 U.S.C. 154(b) by 298 days.

(21) Appl. No.: 15/752,086

(22) PCT Filed: Aug. 11, 2016

(86) PCT No.: PCT/US2016/046639
§ 371 (c)(1),
(2) Date: Feb. 12, 2018

(87) PCT Pub. No.: WO2017/027753
PCT Pub. Date: Feb. 16, 2017

(65) Prior Publication Data
US 2018/0240364 A1    Aug. 23, 2018

Related U.S. Application Data

(60) Provisional application No. 62/203,863, filed on Aug. 11, 2015.

(51) Int. Cl.
*G09B 23/28* (2006.01)
*A61M 5/178* (2006.01)
(Continued)

(52) U.S. Cl.
CPC .......... *G09B 23/285* (2013.01); *A61M 5/178* (2013.01); *A61M 5/31578* (2013.01);
(Continued)

(58) Field of Classification Search
USPC ......... 434/262, 267; 604/134, 135, 192–196, 604/506
See application file for complete search history.

(56) References Cited

U.S. PATENT DOCUMENTS 3,795,061 A * 3/1974 Sarnoff ................ G09B 23/285
434/262
5,318,547 A   6/1994 Altschuler
(Continued)

FOREIGN PATENT DOCUMENTS

WO    2005/009519    2/2005
WO    2014/154795    10/2014
(Continued)

OTHER PUBLICATIONS

International Search Report and Written Opinion for PCT Application PCT/US16/046639 dated Dec. 22, 2016, pp. 1-13.
(Continued)

*Primary Examiner* — Kurt Fernstrom
(74) *Attorney, Agent, or Firm* — Timothy H. Van Dyke; Wolter Van Dyke Davis, PLLC

(57) ABSTRACT

Embodiments provided herein include a resettable injection training device having a body, a plunger slidable relative thereto, an injection simulation member and retractable and extendable shield, wherein the shield releasably locks in a retracted position prior to use. After use of the training device, the shield extends over the injection simulation member to prevent contact with the injection simulation member. Resetting of the slidable shield occurs by applying a force onto a distal end of the shield to retract the shield
(Continued)

until a shield locking surface interacts with a locking surface on the body to maintain the shield in a retracted position. Release of the shield from a retracted position to an extended position may occur by moving the plunger toward a distal end of the body until a contact region at a proximal end of the plunger releases the shield locking surface from the body locking surface to release the shield.

18 Claims, 6 Drawing Sheets

(51) Int. Cl.
*A61M 5/315* (2006.01)
*A61M 5/32* (2006.01)
*A61M 5/31* (2006.01)

(52) U.S. Cl.
CPC ........ *A61M 5/3202* (2013.01); *A61M 5/3221* (2013.01); *A61M 5/315* (2013.01); *A61M 5/3148* (2013.01); *A61M 5/3204* (2013.01); *A61M 5/326* (2013.01); *A61M 5/3243* (2013.01); *A61M 5/3286* (2013.01); *A61M 2005/3261* (2013.01); *A61M 2005/3265* (2013.01)

(56) References Cited

U.S. PATENT DOCUMENTS

| | | | |
|---|---|---|---|
| 5,344,407 A | 9/1994 | Ryan | |
| 5,567,160 A * | 10/1996 | Massino | G09B 23/285 434/262 |
| 7,220,247 B2 | 5/2007 | Shaw et al. | |
| 7,682,155 B2 * | 3/2010 | Raven | G09B 23/285 434/262 |
| 10,417,937 B2 * | 9/2019 | Gaillot | G09B 23/285 |
| 2008/0059133 A1 * | 3/2008 | Edwards | G06Q 10/00 703/7 |
| 2008/0269689 A1 * | 10/2008 | Edwards | A61M 5/2053 604/189 |
| 2010/0160894 A1 * | 6/2010 | Julian | A61M 5/2033 604/506 |
| 2012/0015336 A1 * | 1/2012 | Mach | G09B 23/285 434/262 |
| 2012/0253314 A1 * | 10/2012 | Harish | A61M 5/2033 604/506 |
| 2016/0049098 A1 * | 2/2016 | Swanson | G09B 23/285 434/262 |
| 2016/0293058 A1 | 10/2016 | Gaillot et al. | |
| 2017/0148354 A1 | 5/2017 | Baker et al. | |

FOREIGN PATENT DOCUMENTS

| | | |
|---|---|---|
| WO | 2014/164948 A1 | 10/2014 |
| WO | 2014154795 A1 | 10/2014 |
| WO | 2017027753 A1 | 2/2017 |

OTHER PUBLICATIONS

BD, "BD Safety and Shielding Systems", brochure, 2 pages (2017).
Extended European Search Report for EP Application 16835945.3 dated Feb. 12, 2019, pp. 1-7.
International Search Report and Written Opinion for PCT/US18/59204; dated Feb. 7, 2019, 17 pages.
CN201680057916.8; Office Action; dated Nov. 14, 2019 15 pages.

* cited by examiner

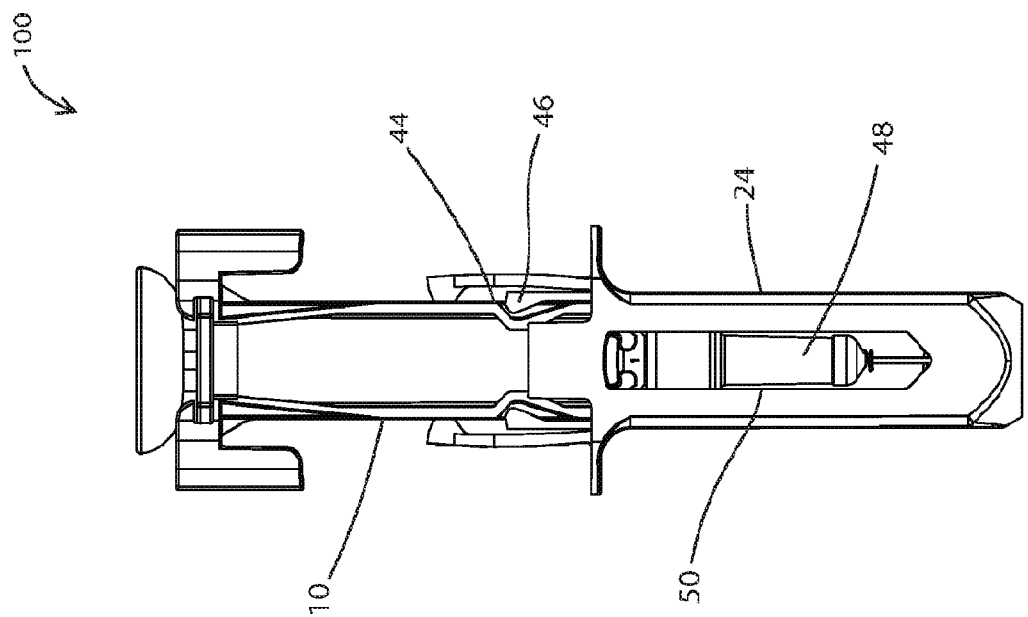
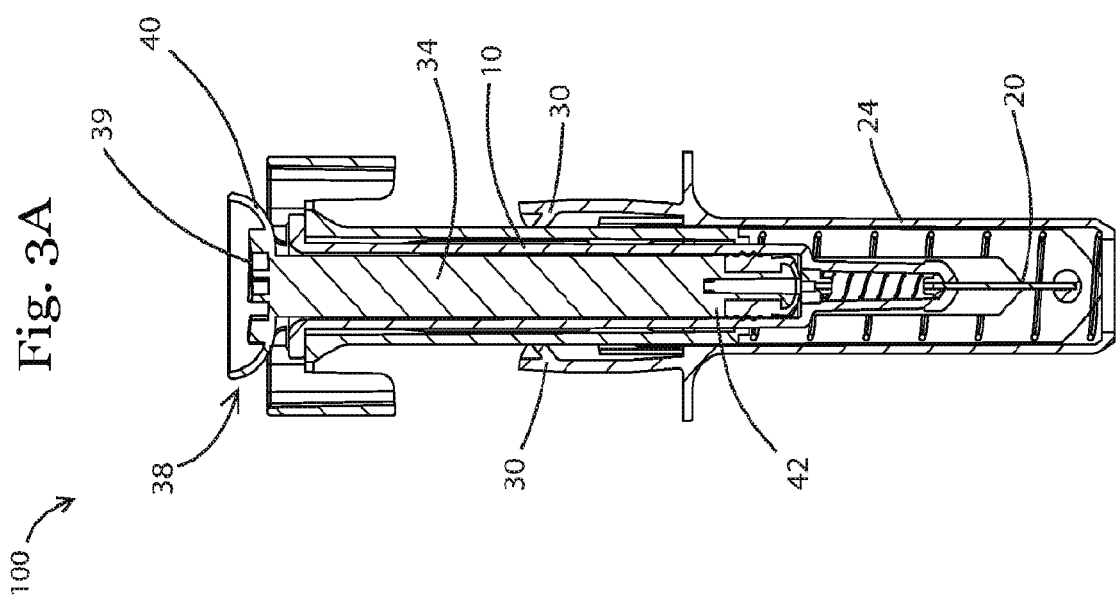

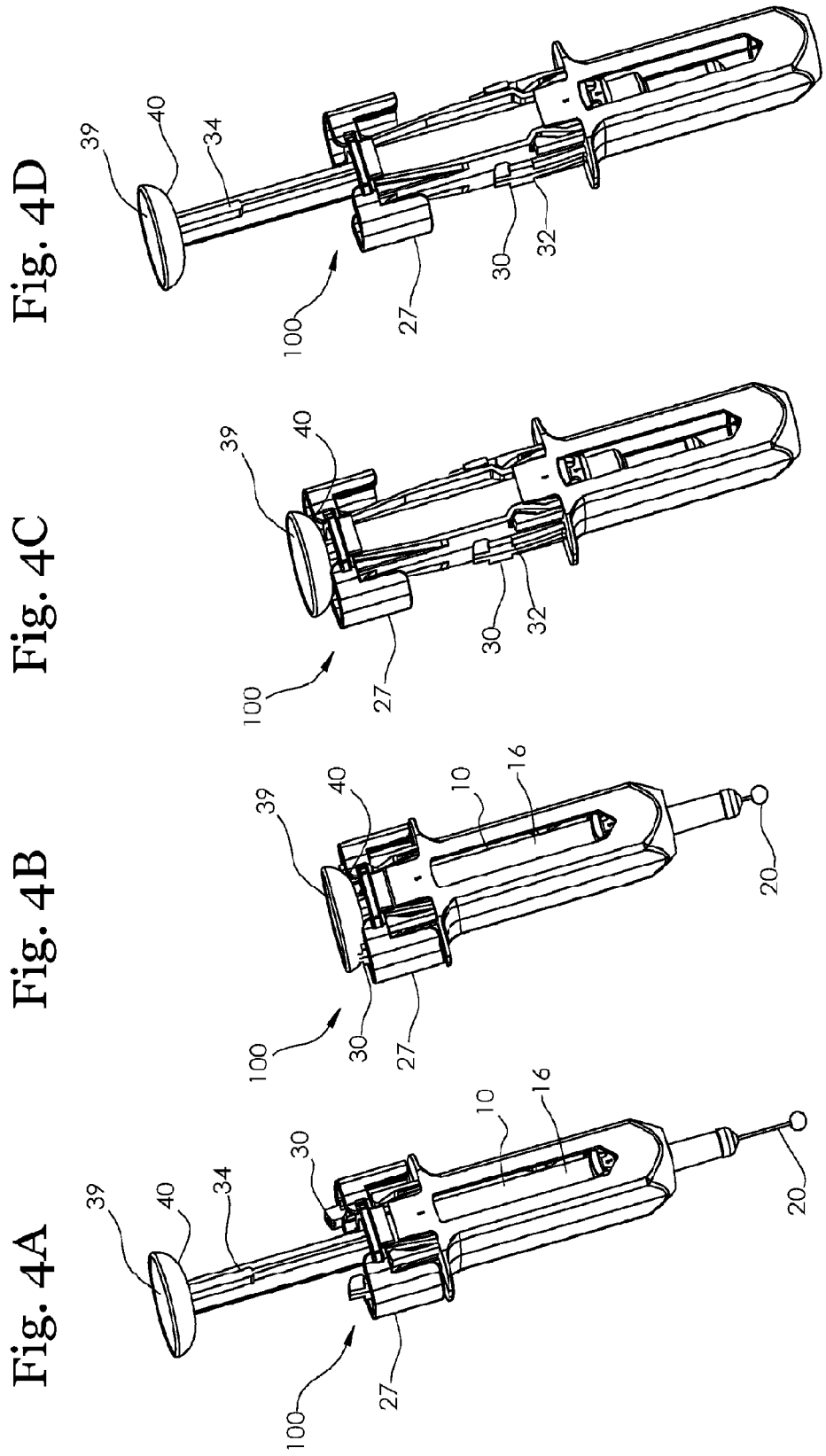

PREFILLED SYRINGE TRAINING DEVICE WITH RELEASEABLY LOCKING NEEDLE GUARD

CROSS-REFERENCE TO RELATED APPLICATIONS

This application claims priority to U.S. Provisional Application No. 62/203,863, filed Aug. 11, 2015.

BACKGROUND

Injection devices have recently become increasingly popular for single dose or multi-dose, at home self-administration. These devices include both auto-injection devices and pre-filled syringe devices, and are often designed to accomplish two basic objectives: convenience of drug delivery in an outpatient or at home setting, and/or automation of drug delivery in an outpatient or at-home setting. These devices may be mechanically spring-loaded devices that advance a plunger or rubber stopper to transfer medication via hollow-bore needle to a patient's tissues, in some examples. These devices lack the ability to regulate whether the medication is actually delivered to the patient or whether it is delivered to a correct location. Most of these devices fail to integrate advanced digital capabilities.

Injectable medications are required for a number of varying illnesses and diseases. A number of injectable medications require self-injection by a patient. Self-injection of a medicament using a device having a needle carries with it a certain stigma. Oftentimes patients are weary of injecting themselves for fear or anxiety related to failing to receive a complete dose of the medication, pain associated with injecting oneself with the needle, accidentally sticking oneself with the needle, and difficulties in adequately grasping the dosing mechanism to inject oneself, among other concerns. These fears and anxieties associated with the currently available self-injection devices may result in the administration of an incomplete dose of a medicament, failure to administer any portion of the dose of a medicament, or accidentally sticking oneself with the needle of the device, which in some instances could lead to unwanted transmission of diseases if the needle is contaminated.

An additional concern exists with regard to injection devices is that users with little or no medical knowledge or experience are injecting themselves or injecting others using these devices. Performing a medical treatment or test on oneself or others carries with it certain risks and often creates a level of anxiety for the user performing the treatment or test. It has proven beneficial in the medical field to practice various medical techniques including drug delivery, specifically where it relates to injections and other invasive drug delivery means prior to delivering the medications to a patient in need, and particularly in the case of self-administration of medicaments. Training devices are helpful in reducing anxiety associated with self-administering medical treatment, as well as increasing efficiency and accuracy in providing the treatment to patients. Medical devices can be intimidating to use; the fear associated with giving oneself an injection, for example, can be traumatic. This fear is increased in persons with little or no experience in self-administration of medications. Consequently, devices to assist in training individuals to inject themselves or otherwise self-administer medication are beneficial in decreasing or preventing the anxiety associated with medicament delivery. In many cases, unfamiliarity with the way in which a particular injection device functions is the cause of concern an anxiety in users, and oftentimes the cause of mistakes when using the device.

Safe use and re-use of these training devices requires resetting of the devices by way of a mechanism that provides the movement of the device to initiate the injection, and in some instances, the portion of the device that protects users from sticking themselves. Therefore, a device which allows repeated practice and use to enhance familiarity with the injection device and the self-injection process, along with the ability to safely and efficiently reset the device is paramount to an effective device for injection training.

SUMMARY

In an embodiment, a resettable injection training device is provided. The device includes a body having a proximal end and a distal end, the body defining a cavity there within. The body includes a body locking surface adjacent to the proximal end. An injection simulation member extends from the distal end of the body, a releasable locking shield having a proximal end and a distal end, the shield being slidably engaged with the body and slidable between a retracted position to expose the injection simulation member and an extended position to cover the injection simulation member is provided. The shield comprising at least one arm having an arm locking surface configured to interface with the body locking surface to releasably lock the shield in the retracted position. A biasing member may be disposed between the distal end of the shield and the distal end of the body, biasing the shield toward an extended position, and a plunger comprising a proximal end and a distal end, the proximal end comprising an end member having a contact region, the plunger being slidable within the cavity, such that a pressure applied to the end member advances the plunger toward the distal end of the body, wherein an interface between the contact region and the at least one arm releases the arm locking surface from the body locking surface to release and extend the shield. The device may optionally include: 1) one or more indentations adjacent to the distal end of the body, and the shield may include one or more interfacing tabs adapted to interface with the one or more indentations in the body to maintain the shield in the extended position, such that the one or more tabs are slidable relative to the one or more indentations upon an application of a force of between 100 Newtons (N) and 0.01 N on the distal end of the shield to retract the shield; or 2) no interfacing tabs on the shield.

In a further embodiment, a method for resetting a resettable injection training device having a body is provided. The device includes a plunger disposed within a cavity of the body, and a shield in an extended position, the shield extending over an injection simulation member, and the shield including at least one arm component, the arm component having a locking surface configured to interface with a locking surface on the body when the shield is in a retracted position. The method further includes sliding the plunger component toward a proximal end of the body of the device, providing a force of between 1.00 N and 0.01 N to a distal end of the extended shield to retract the shield relative to the body to expose the injection simulation member until the locking surface of the shield interacts with the locking surface of the body to releasably lock the shield in the retracted position.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which:

FIG. 3A is a cross sectional view of an embodiment of a resettable injection training device shown in FIG. 3B, wherein a shield is in an extended position.

FIG. 3B is a side view of an embodiment of a resettable injection training device showing a shield in an extended position.

FIGS. 4A-4D include perspective views of a resettable injection training device embodiment, providing non-limiting steps of operation for use of the device. 4 is a cross sectional view of the embodiment of the resettable injection training device shown in FIGS. 3A-B, with a plunger component being re-set in preparation for a subsequent use of the device.

DETAILED DESCRIPTION

Figure 1B:
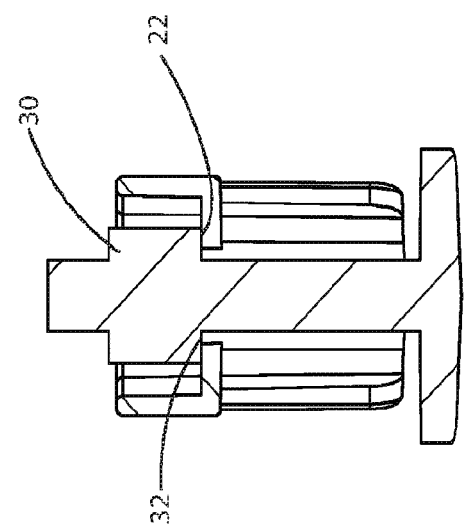
FIG. 1B is a cross sectional view of the embodiment of the resettable injection training device in FIG. 1A taken at x-x.

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another. The modifier "about" used in connection with a quantity is inclusive of the stated value and has the meaning dictated by the context. It is to be noted that all ranges disclosed within this specification are inclusive and are independently combinable.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. As a non-limiting example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 7. As another non-limiting example, a range of "between 20 and 10" can also include the values 20, 10.

The term "adjacent" as used herein, includes but is not limited to near, associated with, or in close proximity to.

Those skilled in the art will understand that the term gauge (G) refers to a gauge of a needle according to gauges known in the art. Typical gauge ranges used in the equation(s) provided herein will include gauges ranging between approximately 18-30.

The inventors herein have identified a need for a device to be used in effectively training patients to use a needle-containing injection device, particularly when these injection devices are used for at home or outpatient environments. In the field of medicament injection training devices, correct injection of medicament by way of the injection device is crucial for obtaining accurate doses of medicament contained therein. Factors such as a fear of needles, fear of pain associated with an injection, inexperience with injection devices and delivering injections, and unfamiliarity with injection devices and their operation, among other factors can contribute to issues in administering the medicament correctly with the injection device. Consequently, patient training in correct operation of the injection device is crucial to reducing patient anxiety and enhancing patient compliance.

During an injection, a user of an injection device having a needle encounters various threes. Oftentimes, the first force encountered is that which is required to traverse a first layer of tissue (oftentimes the skin) with the needle, the pressure required by the user on the needle until the needle traverses the user's first layer of tissue is called a deformation force, which is the force that deforms the skin until the needle punctures the skin. This three required increases as the skin becomes deformed. Following the deformation force, there is often a temporary and typically brief decrease in force on the needle during an injection, known as the puncture force, which is the force that occurs once the needle has traversed the skin, i.e., punctured the skin, and before the needle moves further into the tissue of the patient. A third three often encountered during an injection follows the puncture force, and is termed an insertion force. The insertion force is an increasing force on the needle as the needle traverses tissue of the patient to reach a target location in the patient required for the injection. The increase in force over time typical of the insertion force period occurs as the needle travels through the tissue and can be attributed to an increase in pressure on the needle as it passes through multiple layers of tissue on its trajectory to the target injection location in the patient. These forces are often surprising and unexpected to an inexperienced injection provider, whether it is a patient who is self-administering an injection or a medical personnel administering an injection to a patient. Embodiments of the invention as described herein are provided to accurately simulate these forces, among other features of an injection and an injection device to decrease anxiety associated with administering an injection.

In an embodiment, a injection simulation member is provided to allow for a simulated injection experience without puncturing the skin of a user. The resettable injection training device may include an injection simulation member which may have a blunt end probe or other similar object known in the art provided to mimic the sound, look, and/or feel of the injection by an injection member (i.e., needle, for example) in a training or simulation session allowing a user to train oneself for administering an injection without puncturing the skin of the user. One skilled in the art would realize that the injection simulation member can be made of any materials known in the art to, in some embodiments, provide a flexibility, and tensile modulus to simulate a needle while maintaining the rigidity and stability to provide a simulated sensation of an injection without traversing the skin of a user. The resettable injection training device provides a perception to a user of injection into the skin and mimics or simulates an actual injection during retraction of the injection simulation member from an extended position to a retracted position, in some embodiments, upon application of a force, to simulate an injection without traversing or puncturing the skin of the user.

Embodiments of the resettable injection training device may provide tactile, visual, and auditory stimuli to a user, wherein during use of the device, the tactile, visual, gustatory, olfactory, or auditory feedback, or any combination thereof, are synchronized in a manner such that a needle-containing injection delivery device is accurately simulated. The synchronization of the stimuli is a significant factor in facilitating multisensory learning of the user.

The injection simulation device embodiments described herein may include components which provide a tactile/force reflecting mechanism (i.e., resistance mechanism) to provide force feedback to simulate the feel of an injection device used during an injection. Force feedback is typically accomplished by a tactile/force reflecting mechanism that imparts force to a user of the injection simulation device in response to manipulation of the injection simulation device. The force(s)/resistances that may be generated as a user manipulates the injection simulation device against a surface simulate the forces/resistances encountered during an injection at a target location of a user.

Multiple forces are encountered during an injection, and these forces are often influenced by one or more variables including needle gauge, needle length, injection angle needle point, needle coating or other surface characteristics, lubrication of needle or injection site, needle depth in patient tissue, type of patient tissue (i.e., skin, muscle), characteristics of patient tissue Which may be influenced by age, health, weight, and/or genetically determined variables, among other potential force-influencing variables.

Forces that may be encountered during an injection are simulated in embodiments of the injection simulation device provided herein. Forces that may be encountered during an injection include a deformation force, a puncture rebound force, an insertion force, a relaxation force, and an extraction force or any combination thereof. A deformation force may occur when a needle is pressed onto a surface of a tissue, for example, an outer surface of the epidermal layer of a patient, causing the epidermis to deform under the pressure of the needle prior to puncture of the epidermis by the needle. A puncture rebound force refers to the force that is sensed once the needle traverses the tissue of the subject. It has been discovered that this causes a temporary decrease in force during an injection. An insertion force can be described as the force of the injection after the needle traverses the tissue, and until the needle reaches its target depth in the patient tissue. In some instances, the insertion force is the greatest increase in force over time during the course of an injection. A relaxation force typically follows the insertion force. The relaxation force occurs once the needle has reached its target depth in the patient tissue and the medicament is injected into the target tissue. The relaxation force is marked by a decrease in force that occurs as the medicament is expelled through the needle. An extraction force is one Which is felt during removal or retraction of the needle from the tissue, and is marked by a greater decrease in force over time than the relaxation force, in some non-limiting instances.

Embodiments of the resistance mechanism described herein may include different components in different embodiments. In non-limiting embodiments, the resistance mechanism may include multiple components, such as, a combination of structural features of the injection simulation member which may move relative to one another to produce a resistance during a simulated injection which mimics the forces encountered by a user during an injection with an training device, for example. The resistance produced may be controlled by manipulating the shape(s) of one or more of the structural features, or the surface(s) characteristics of the one or more structural features, or the material(s) of the one or more structural features, in non-limiting embodiments.

The resistance mechanism may alternatively include a material traversable by a needle, for example, to produce a varying resistance to mimic the forces and the tactile feel of an injection. This traversable material may be disposed within the housing of the injection training device or on an outer portion thereof. Traversal of the needle through the traversable material may provide a tactile feel of a needle traversing a tissue of a subject during an injection. Furthermore, the traversal may be viewable by the user of the device, providing a visual and tactile representation to simulate an injection event. The material may include a rubber or septum material, or a pseudo-skin material, in non-limiting embodiments, to further enhance the simulation of penetrating tissue.

In one embodiment, the injection simulation member may configured to simulate a needle of an injection device with a determined gauge (G) and which device is configured such that the injection simulation member retracts from an extended position to a first retracted position under application of a force 1 (N), to simulate a deformation force (Forced) according to the formula Forced=C (−0.046(G)+ 1.83), wherein the force value ranges between +/−1%-30% and every integer in between, and wherein C comprises a coefficient, said coefficient being a factor of the deformation force of the injection simulation device. In another embodiment, the force value ranges +/−1%-20% and every integer in between. In yet another embodiment, the force values ranges +/−1%-10% and every integer in between. The value of C is further defined below. In one non-limiting embodiment, the value of C may include a value between 0.2-3.6.

In a further embodiment, the retraction of the injection simulation member from the extended position to the first retracted position comprises a force determined by the formula F(x)=K*XP wherein F(x) is a force value at a point between the fully extended position and the first retracted position, K is a resistance value including a resistance of the injection simulation device, X is a displacement value, and P is an exponential power value greater than zero. F(x) may be a force value simulating a deformation force in one embodiment. In another embodiment, F(x) may be a force value simulating an insertion force.

In an alternative non-limiting embodiment, F(x) is a force value at a point between the fully extended position and at least a second retracted position. F(x) denotes F as a function of (x). In non-limiting embodiments described herein, F(x) denotes a Force at point x.

In another embodiment, the injection simulation device is provided wherein the deformation force Fd depends on one or more factors including: a composite area of injection value (C1), a bevel of the needle value (C2), lubrication of the needle or an injection site value (C3), and/or injection angle (C4) wherein a force of the device is determined by the formula C=C1*C2*C3*C4*C5.

In one embodiment, the C1 value includes a higher value when the composite area of injection includes a more dense tissue area and a lower value when the composite area of injection includes a less dense tissue area. For example, muscle tissue includes a more dense tissue than in adipose tissue; consequently, the C1 value would be higher for muscle tissue than it would be for adipose tissue. In one non-limiting example, when the composite area of injection includes a subcutaneous tissue, the C1 value ranges from 0.5-2.0.

In a further embodiment, the injection simulation device may be configured to simulate a three based on a needle bevel, wherein the C2 value is higher when a needle with a bevel that creates a larger angle at a distal end of the needle is simulated, and lower when a needle with a bevel that creates a smaller angle at, the distal end of the needle is simulated. In a non-limiting example, the C2 value ranges from between 0.5-1.5.

In still a further embodiment, the injection simulation device may be configured to simulate a force based on lubrication or non-lubrication of a needle or an injection site, and wherein the C3 value is higher when an un-lubricated needle and/or injection site is simulated and lower when a lubricated needle and/or injection site is simulated. In one non-limiting example, the C3 value ranges from between 0.5-1.0.

In yet a further embodiment, the C4 value decreases when a longitudinal axis of the injection simulation member is generally perpendicular to a plane in which a surface including the injection site is disposed, and increases when an angle between the longitudinal axis of the injection simulation member and the plane in which the surface including the injection site decreases. In a non-limiting example, the C4 value includes 1.0 when the angle between the longitudinal axis of the injection simulation member and the plane of the surface including the injection site comprises 90 degrees. In another non-limiting example, the C4 value includes 1.4 when the angle between the longitudinal axis of the injection simulation member and the plane of the surface including the injection site comprises 45 degrees.

The exponential value, is a value that may affect the change in three exponentially, where as the P value increases, the force value may increases exponentially. In a non-limiting embodiment, the P value may range between 0.5 and 4.

The displacement value, X, is a position of the injection simulation member as it moves between extended and retracted positions. In one non-limiting embodiment, the X value ranges between 0.000001 mm and 250 mm.

In an embodiment, an injection training device for simulating one or more forces of an injection may include a retractable injection simulation member configured to simulate a needle of an injection device with a determined gauge. The device is configured such that the injection simulation member retracts from an extended position to a retracted position upon application of a force according to a multi-phase force profile. The multi-phase force profile may include at least a first phase configured to simulate a deformation force, the deformation force simulating the force of pressing a needle against a subject so as to deform at least a first layer of tissue prior to puncturing at least the first layer of tissue of the subject; and at least a second phase configured to simulate a puncture rebound force, in a non-limiting embodiment. In one embodiment, the second phase includes a force that is less than the deformation force.

The device may further include at least a third phase configured to simulate an insertion force, wherein the insertion force includes the force required for a needle to traverse the tissue to a target injection location of the subject. The target injection location includes a location wherein the injection is to occur, such as, muscular tissue, intra-ocular tissue, subcutaneous tissue, adipose tissue, intra or inter peritoneal tissue, inter or intra venous or arterial tissue, among other target locations for injections known to those skilled in the art.

In a further embodiment, the injection simulation device includes one or more additional phases configured to simulate puncturing of composite tissue areas. Composite tissue areas may include multiple layers of tissue that may be traversable, wherein multiple deformation, puncture, and insertion forces are required to reach the target location for the injection. Certain procedures such as an amniocentesis, for example, used in prenatal diagnosis of chromosomal abnormalities, fetal infections, or sex determination from a sample of amniotic fluid containing fetal tissues retrieved from the amniotic sac using a needle in the procedure, require passage through multiple layers of tissue to reach the target location. These procedures may include multiple phases and multiple forces which are experienced and which may be simulated in embodiments of the injection simulation device provided herein.

Figure 5:
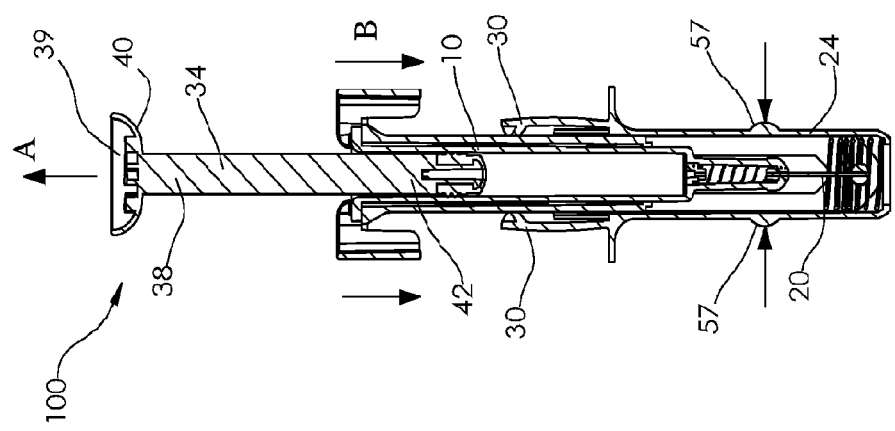
FIG. 5 is a cross sectional view of the embodiment of the resettable injection training device shown in FIGS. 3A-B, and 4D with the safety shield in an extended position, indicating steps to reset the device.

The locking mechanism may include a mechanism to maintain the shield in an extended position. This locking mechanism may be unlocked to release the shield to be retracted for resettable, multi-use devices. In one embodiment, the locking mechanism may include body indentations on the device body and interfacing tabs associated with the shield, such that an interaction between the interfacing tabs and the indentations allows the shield to be retained in an extended, locked position. An unlocking mechanism may release the shield tabs from the indentations on the body, such that the shield may be retracted for a subsequent use. The unlocking mechanism may include a portion of the device that is compressed which allows release of another portion of the device which includes release of the tabs from the indentations, in one embodiment. For example, the portion of the device that is compressed may include a designated portion of the shield or the device housing, or may include a button associated with the device in non-limiting embodiments. The button or component on the device may be actuated to release the locking mechanism, for example. This unlocking mechanism may include a region of the shield that is compressed (as shown in FIG. 5) to cause the locking tabs to be released from the indentations on the body. In another embodiment, the locking mechanism may be released, or unlocked, by movement of the plunger relative to the body such that the locking mechanism is released, the locking tabs are released from the indentations, and the shield is retractable.

Figure 1A:
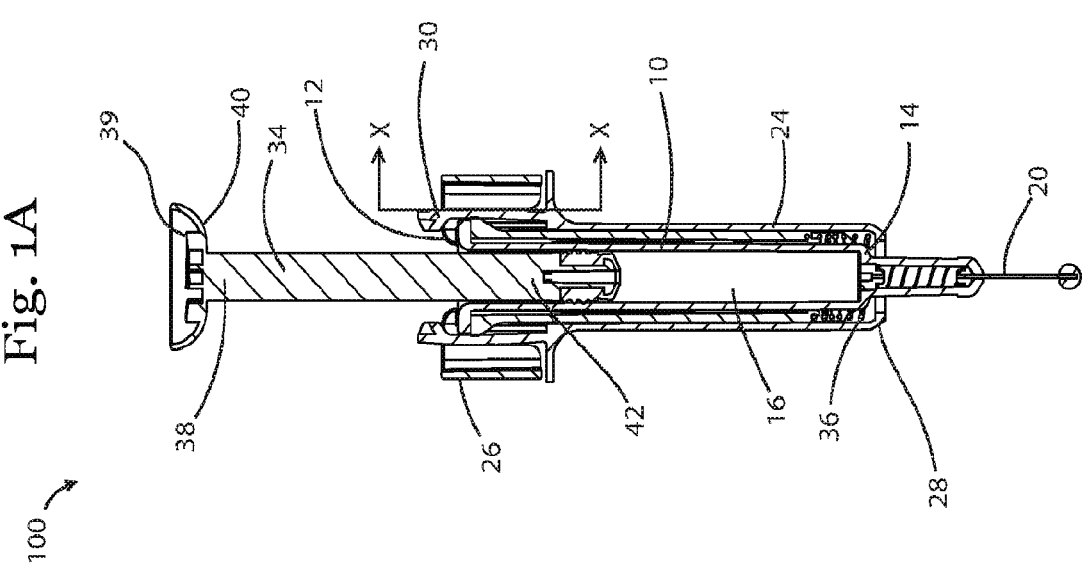
FIG. 1A is a cross sectional view of an embodiment of a resettable injection training device.

Turning to the Figures, FIG. 1A is a cross sectional view of an embodiment 100 of a resettable injection training device having a body 10 with a proximal end 12 and a distal end 14. A cavity 16 is defined within the body 10 and an injection simulation member 20 extends from the distal end of the body 10. A body locking surface 22 is provided near the proximal end of the body as shown in the partial sectional view of FIG. 1B taken at axis X-X of FIG. 1A. A releaseable locking shield 24 having a proximal end 26 and a distal end 28 is slidably engaged with the body 10. The shield 24 is slidable between a retracted position, exposing the injection simulation member as shown in FIG. 1A, and an extended position as shown in FIGS. 3A-B, extending over the injection simulation member 20. The shield includes at least one arm portion 30 (two arm portions are shown in FIG. 1A), and the arm portion 30 includes an arm locking surface 32 (shown in 1B). The arm locking surface 32 interfaces with the body locking surface 22 to maintain the shield 24 in the retracted position until its release as described below.

The device 10 further includes a plunger 34 slidable relative to the cavity 16, and a biasing member 36 disposed between the distal end 28 of the shield 24 and the distal end 14 of the body 10, in one non-limiting embodiment, biasing the shield toward an extended position. In other non-limiting embodiments, the biasing member 36 may be disposed in other locations of the device to provide the same function as that described in the embodiment shown in the Figures herein. The plunger 34 has a proximal end 38 and a distal end 42, an end member 39 and a contact region 40 at the proximal end 38. In one non-limiting embodiment, the end member 39 may form the contact region 40, in another non-limiting embodiment, the plunger 34 may form a contact region 40 at its proximal end 38.

Figure 2:
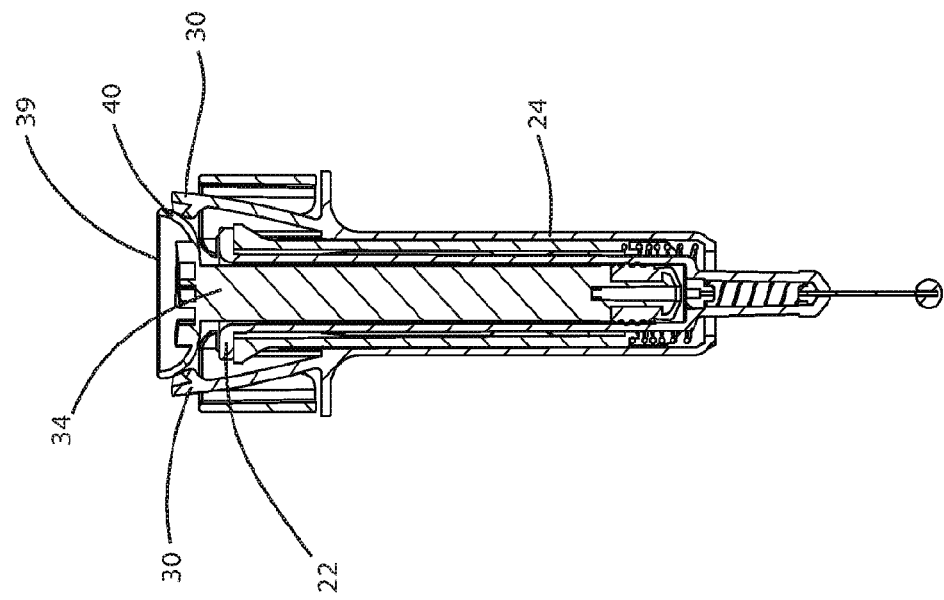
FIG. 2 is a cross sectional view of the embodiment of the resettable injection training device of claim 1, wherein the device has been activated and a releasable locking mechanism has been released.

During use of the device, the contact region 40 is adapted to contact the one or more arms 30 of the device when the plunger 34 is urged toward the distal end 14 of the body 10. The distal end of the plunger 42 may include or be coupled to a stopper, in non limiting embodiments. Movement of the plunger toward the distal end 14 of the body 10 simulates movement of a plunger in a drug delivery-needle containing device to deliver medicament from the device. Movement of the plunger 34 toward the distal end 42 of the body 10 causes the contact region 40 to contact the one or more arms 30 of the shield 24 causing lateral movement of the arms 30 and releasing the arm locking surface 32 of each arm from the body locking surface 22 as shown in FIG. 2. Release of the arm locking surface 32 from the body locking surface 22 unlocks the shield 24, allowing the shield 24 to be released from the locked position. Once released, the shield 24 can extend over the injection simulation member 20, as shown in the cross sectional view of FIG. 3A.

FIG. 3B shows a side view of the device embodiment 100 shown in the cross sectional view of FIG. 3A with the shield 24 in an extended position. In one non-limiting embodiment, the body 10 may include one or more indentations 44, which may be configured interact with one or more interfacing tabs 46 of the shield 24 when the shield 24 is in an extended position. In this non-limiting embodiment, the tabs 46 interface with the indentations 44 in the body 10 to maintain the shield 24 in the extended position. These tabs 46 may be slidable relative to the indentations 44 to allow the shield 24 to retract, in one embodiment. A force threshold of between 100 Newtons (N) and 0.01 N must be overcome to retract the shield 24 in one non-limiting embodiment. In one embodiment, between 100-0.01 N of force must be overcome in order to slide the interfacing tabs 46 relative to the indentations 44 and retract the shield 24 and expose the injection simulation member 20. In other non-limiting embodiments, the body may not include the indentations 44 and the shield may not include the interfacing tabs 46, but may instead include other configurations for locking and unlocking the shield 24 of the device. In other embodiments, forces of between 75 N and 0.001 N, between 50 N and 0.01 N or between 25 N and 0.01 N may be required to effectively retract the shield 24, in non-limiting embodiments.

In the non-limiting embodiment shown in FIG. 3B, the body 10 may include a transparent portion 48 to allow a user to see the contents of the body 10 and into the cavity 16. In an alternative embodiment, the body 10 may include an opening providing a view into the contents of the body 10. In another non-limiting embodiment, other portions or the entire body 10 may be formed of a transparent material, or may have openings throughout the body 10 to provide a view of the interior contents of the body 10 before, during, or after operation of the device. In still a further non-limiting embodiment, a window 50 may be provided in a portion of the shield 24 to allow a user to view the body 10 when the shield 24 is in an extended position, as shown in FIG. 3B. These features may allow a user to determine an amount of fluid in the cavity 16, for example, during use of the device in embodiments where a fluid is contained within the cavity 16. In other embodiments, the transparent portion or window 48 may allow a user to see the location of one or more components of the device to determine the position of the components during use of the device.

Turning to FIGS. 4A-4D, to use the device 100 in a training event, the injection simulation member 20 is placed against a target surface of a user, in one embodiment, the injection simulation member 20 includes a biasing member (injection member biasing member shown in FIGS. 3A-B and FIG. 5) allowing it to be compressed as the device is pressed against the user as shown in FIG. 4B. The injection simulation member 20 may include a rounded portion at its distal end as shown in the embodiments provided herein, but this embodiment is not intended to be limiting in scope. The injection simulation member may include any shape or size to prevent puncture of the skin of a user during use of the device. In another embodiment, the injection simulation member may include a blunted end, for example. The device further includes a flange portion 27 and a plunger 34, the plunger 34 can be moved into the cavity 16 toward the flange portion 27 by pressing upon the proximal region of the plunger 34 (or in some embodiments, on the end member 39). The plunger 34 is moved toward the flange portion 27 until the contact region 40 abuts the arm portions 30 of the shield as shown in FIG. 4B. The arms 30 of the shield 24 are displaced from the body 10 such that the arm locking surface 32 is displaced from the body locking surface 22, releasing the shield 24 from the locked position as shown in FIG. 4C to the unlocked position, such that the shield is urged to an extended position as shown in FIG. 4C. A biasing member 36 (biasing member 36 is shown in FIGS. 1A, 2, 3A-3B) may be included to provide the three to extend the shield to as the position shown in FIG. 4C. The plunger 34 may then be moved relative to the cavity 16 toward the proximal end of the device 10 and away from the flange 27 as shown in FIG. 4D. The shield 24 may be removably or permanently locked in the extended position shown in FIG. 4C-4D, in non-limiting embodiments.

To reset the device 10 for a subsequent use, the shield 24 is retracted, to expose the injection simulation member 20. The plunger 34 can be moved away from the flange 27 of the device 10, as shown by arrow A in FIG. 5 (also shown in FIG. 4D). Movement of the flange 27 relative to the plunger as shown by arrow B or movement of the plunger away from the flange as shown by arrow A, or both may occur. The shield 24 may then be reset to a retracted position. A threshold force of less than 100 Newtons may overcome the extended position of the shield 24, in a non-limiting embodiment. Once the arm locking surface 32 interfaces with the body locking surface 22 (shown in FIG. 1B, FIG. 4C, FIG. 4D) the shield 24 is releasably locked in a retracted position, and the device 10 may be used in a subsequent training. In one non-limiting embodiment, when the shield 24 is in the extended and locked position, to reset the shield 24, and release the interfacing tabs 46 (see FIG. 3B) from the body indentations 44 (see FIG. 3B), depressing a portion of the shield may cause the interfacing tabs 46 to be displaced from the body indentations 44 to reset the shield. As shown in 5, this portion of the shield which may be depressed may include one or more compressible components 57 on the outer surface of the shield 24, in one non-limiting embodiment. In other examples, the device may include markings on an outer surface of the shield 24, indicating a position on the shield to be depressed by the user to release the locking mechanism and reset the shield 24.

Figure 6A:
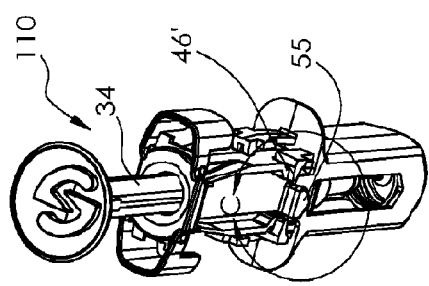
FIG. 6A is a side perspective view of a resettable injection training device embodiment with a shield in an extended position.
Figure 6B:
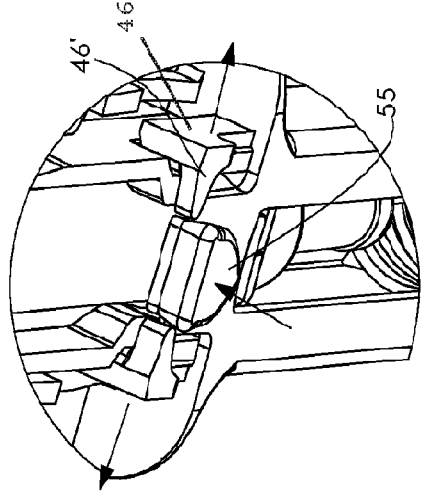
FIG. 6B is a partial sectional view of the training device of FIG. 6A taken at section A.
Figure 6C:
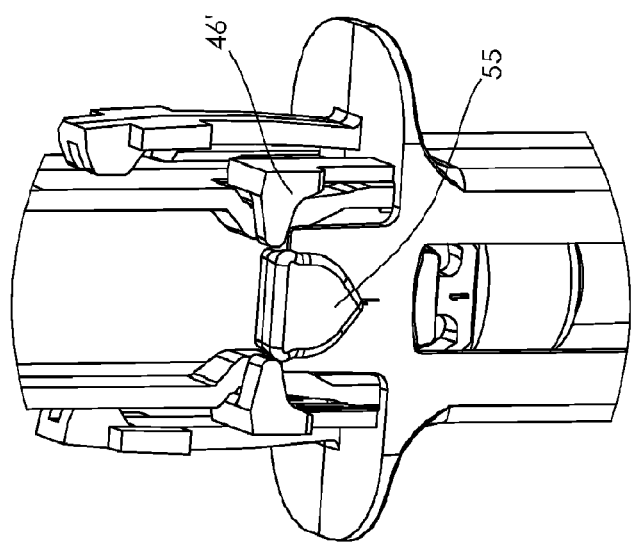
FIG. 6C is a partial sectional view of the training device of FIG. 6D taken at section C.
Figure 6D:
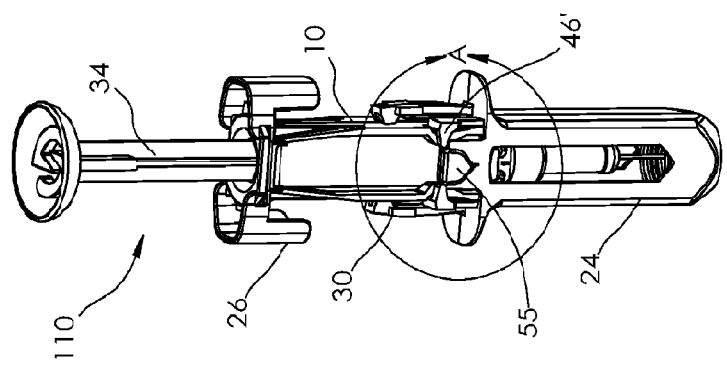
FIG. 6D is a top perspective view of the resettable injection training device embodiment of FIG. 6A.

In a further embodiment, shown in FIGS. 6A-6D, a resettable injection training device 110 having a body 10, a plunger 34, and a shield 24 is provided. In the perspective views of FIGS. 6A and 6D, the shield 24 is shown in an extended position. Partial sectional view 6B is taken from section A of FIG. 6A, and partial sectional view 6C is taken from section C of FIG. 6D. An unlocking member 55 is provided on a portion of the shield 24. The shield 24 includes interfacing tabs 46 (as shown in FIGS. 3B and 6C), which interface with body indentations 44 (also shown in FIG. 3B) to form the locking mechanism to lock the shield 24 in an extended position as shown in FIG. 6A, in one non-limiting embodiment. The interfacing tabs 46 may be associated with unlocking tabs 46' such that movement of unlocking tabs 46' may cause interfacing tabs 46 to be released from the body indentations to release the shield 24 from its extended, locked position. The unlocking member 55 may include a depressible element, such as a button, in a non-limiting embodiment, and may include tapered edges as shown in the sectional view of FIG. 6C, in some non-limiting embodiments. When the shield 24 is in an extended and releasably locked position as shown in FIGS. 6A-D, depression of the unlocking member 55 may cause an interaction between one or more unlocking tabs 46' and the unlocking member 55 of the shield 24, causing the unlocking tabs 46' to be moved outward in a lateral direction relative to the body of the device (as indicated by the arrows in FIG. 6C), which causes release of the interfacing tabs 46 from the body indentations 44 to release the shield 24 from the locked position. The shield 24 can then be retracted by moving the shield 24 toward the proximal end of the device 10.

In another non-limiting example, the plunger 34, may include an unlocking member feature, such that when the plunger 34 is moved away from the flange portion 27 of the device shown in FIG. 6A (i.e., by pulling the plunger partially out of the cavity of the device as also shown by arrow A in FIG. 5), the unlocking member feature (not shown) on the plunger 34 may cause movement of the unlocking tabs 46' and/or the interfacing tabs 46, releasing the tabs from the body indentations 44 so as to allow the shield 24 to be retracted for a subsequent use of the device.

In some other non-limiting embodiments, the shield 24 may be permanently locked such that the device may be a one-time use device. However, in other non-limiting embodiments as described herein, the device 10 may be a multi-use training device, as described in embodiments herein, and therefore, unlocking or releasing of the extended shield 24 can occur to allow for multiple uses of the device 10.

In another non-limiting embodiment, a method for resetting a resettable injection training device is provided, the device having a body, a plunger disposed within a cavity of the body, and a shield in an extended position, the shield extending over an injection simulation member, the shield comprising at least one arm component, and the arm component comprising a locking surface configured to interface with a locking surface on the body when the shield is in a retracted position. The method further includes sliding the plunger component toward a proximal end of the body of the device, and providing a force of between 100 N and 0.01 N to a distal end of the extended shield to retract the shield relative to the body to expose the injection simulation member until the locking surface of the shield interacts with the locking surface of the body to releasably lock the shield in the retracted position.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. As a non-limiting example, a range of "less than 10" can include any and all sub-ranges between and including) the minimum value of zero and the maximum value of 10, that is, any and all sub-ranges having a minimum value of equal to or greater than zero and a maximum value of equal to or less than 10, e.g., 1 to 7.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation,

What is claimed is:

1. A resettable injection training device, comprising:
a body comprising a proximal end and a distal end, the body defining a cavity there within, the body having a body locking surface adjacent to the proximal end;
an injection simulation member extending from the distal end of the body;
a releasable locking shield comprising a proximal end and a distal end, the shield being slidably engaged with the body and slidable between a retracted position to expose the injection simulation member and an extended position to cover the injection simulation member, the shield comprising at least one arm having an arm locking surface configured to interface with the body locking surface to releasably lock the shield in the retracted position;

a biasing member disposed between the distal end of the shield and the distal end of the body, biasing the shield toward an extended position;

a plunger comprising a proximal end and a distal end, the proximal end comprising an end member having a contact region, the plunger being slidable within the cavity, such that a pressure applied to the end member advances the plunger toward the distal end of the body, wherein an interface between the contact region and the at least one arm releases the arm locking surface from the body locking surface to release and extend the shield;

wherein proximal movement of the shield relative to the body retracts the shield to reset the device for being used in a subsequent injection training; and wherein the device optionally includes: 1) one or more indentations adjacent to the distal end of the body, and the shield comprises one or more interfacing tabs adapted to interface with the one or more indentations in the body to maintain the shield in the extended position, such that the one or more tabs are slidable relative to the one or more indentations upon an application of a force of between 100 Newtons and 0.01 Newtons on the distal end of the shield to retract the shield; or 2) no interfacing tabs on the shield.

2. The resettable injection training device of claim 1, wherein the body comprises at least a transparent portion adjacent to the cavity to allow a user to view inside the cavity.

3. The resettable injection training device of claim 2, wherein the shield comprises a window disposed between the proximal and distal end of the shield, at least a portion of the window configured to align with at least a portion of the transparent portion of the body to provide a view inside of the cavity once the shield is moved from the extended position toward the retracted position.

4. The resettable injection training device of claim 1, wherein the injection simulation member is configured to simulate a needle of an injection device with a determined gauge (G) and which device is configured such that the injection simulation member retracts from an extended position to a first retracted position under application of a $force_1$ (N), to simulate a deformation force ($Force_d$) according to the following formula:

$$Force_d = C(-0.046(G)+1.83)$$

wherein the force value ranges between +/−1%-30% and every integer in between, and wherein C comprises a coefficient, said coefficient being a factor of the deformation force of the injection simulation device.

5. The resettable injection training device of claim 1, wherein the one or more tabs are slidable relative to the one or more indentations upon an application of a force of between 75 Newtons and 0.01 Newtons on the distal end of the shield to retract the shield.

6. The resettable injection training device of claim 1, wherein when the device comprises one or more indentations adjacent to the distal end of the body and the shield comprises one or more interfacing tabs adapted to interface with the one or more indentations in the body to maintain the shield in the extended position, the one or more tabs are slidable relative to the one or more indentations upon an application of a force of between 50 Newtons and 0.01 Newtons on the distal end of the shield to retract the shield.

7. The resettable injection training device of claim 1, wherein when the device comprises one or more indentations adjacent to the distal end of the body and the shield comprises one or more interfacing tabs adapted to interface with the one or more indentations in the body to maintain the shield in the extended position, the one or more tabs are slidable relative to the one or more indentations upon an application of a force of between 25 Newtons and 0.01 Newtons on the distal end of the shield to retract the shield.

8. A resettable injection training device comprising:
a body comprising a proximal end and a distal end, and a body locking surface adjacent to the proximal end;
an injection simulation member extending from the distal end of the body;
a plunger slidable relative to the body, the plunger comprising a proximal end and a distal end, the proximal end comprising an end member having a contact region;
a releasable locking shield having a proximal end and a distal end, the shield being slidably engaged with the body, the shield being slidable between an extended position and a retracted position, said shield comprising at least one arm member comprising a locking arm surface configured to interface with the body locking surface when the shield is in a retracted position;
a biasing member disposed between the distal end of the shield and the distal end of the body, biasing the shield toward an extended position;
wherein an interface between the contact region of the plunger and the at least one arm displaces the locking arm surface from the body locking surface to release the releasable locking shield and allow the shield to be extended;
a releasable locking mechanism associated with the releasable locking shield and the body or the plunger, or both, to secure the shield in the extended position; and
wherein reset of the device occurs by proximal movement of the shield relative to the body to retract the shield to reset the device for use in a subsequent injection training.

9. The resettable injection training device of claim 8, wherein the injection simulation member is configured to simulate a needle of an injection device with a determined gauge (G) and which device is configured such that the injection simulation member retracts from an extended position to a first retracted position under application of a $force_1$ (N), to simulate a deformation force ($Force_d$) according to the following formula:

$$Force_d = C(-0.046(G)+1.83)$$

wherein the force value ranges between +/−1%-30% and every integer in between, and wherein C comprises a coefficient, said coefficient being a factor of the deformation force of the injection simulation device.

10. The resettable injection training device of claim 8, wherein the releasable locking mechanism comprises one or more interfacing tabs extending from the shield, wherein the one or more interfacing tabs are adapted to interact with the body to secure the shield in the extended position.

11. The resettable injection training device of claim 10, wherein the body comprises one or more indentations on adapted to receive the one or more interfacing tabs when the shield is in an extended position, to lock the shield in the extended position.

12. The resettable injection training device of claim 11, further comprising an unlocking member associated with the shield or body, or both, such that the unlocking member interacts with the one or more interfacing tabs, wherein activation of the unlocking member causes the one or more interfacing tabs to release the locking mechanism such that the shield can be retracted.

13. The resettable injection training device of claim 12, wherein the interfacing tabs comprise unlocking tabs that interact with the unlocking member wherein activation of the unlocking member, moves the interfacing tabs via interaction of the unlocking member and unlocking tabs to release the shield from the locked, extended position.

14. The resettable injection training device of claim 11, further comprising an unlocking member associated with the plunger, and wherein movement of the plunger away from the body of the device activates the unlocking member, moving the unlocking member relative to the interfacing tabs to release the interfacing tabs such that the shield can be retracted from an extended position.

15. A method for resetting a resettable injection training device having a body, a plunger disposed within a cavity of the body, and a shield in an extended position, the shield extending over an injection simulation member, the shield comprising at least one arm component, the arm component comprising a locking surface configured to interface with a locking surface on the body when the shield is in a retracted position, the method comprising:
 sliding the plunger component toward a proximal end of the body of the device;
 providing a force of between 100 N and 0.01 N to a distal end of the extended shield to retract the shield relative to the body to expose the injection simulation member until the locking surface of the shield interacts with the locking surface of the body to releasably lock the shield in the retracted position.

16. The method of claim 15, wherein a force of between 75 N and 0.01 N applied to the distal end of the extended shield retracts the shield.

17. The method of claim 15, wherein a force of between 50 N and 0.01 N applied to the distal end of the extended shield retracts the shield.

18. The method of claim 15, wherein a force of between 25 N and 0.01 N applied to the distal end of the extended shield retracts the shield.

* * * * *